US010912604B2

(12) United States Patent
Manstein

(10) Patent No.: US 10,912,604 B2
(45) Date of Patent: *Feb. 9, 2021

(54) METHOD AND APPARATUS FOR DERMATOLOGICAL TREATMENT AND TISSUE RESHAPING

(71) Applicant: The General Hospital Corporation, Boston, MA (US)

(72) Inventor: Dieter Manstein, Miami, FL (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/844,597

(22) Filed: Dec. 17, 2017

(65) Prior Publication Data

US 2018/0103998 A1   Apr. 19, 2018

Related U.S. Application Data

(60) Continuation of application No. 14/725,976, filed on May 29, 2015, now Pat. No. 9,877,778, which is a
(Continued)

(51) Int. Cl.
*A61B 18/18*  (2006.01)
*A61B 18/14*  (2006.01)
(Continued)

(52) U.S. Cl.
CPC .......... *A61B 18/1477* (2013.01); *A61B 18/18* (2013.01); *A61M 5/158* (2013.01);
(Continued)

(58) Field of Classification Search
CPC .......... A61B 18/00; A61B 2018/00005; A61B 2018/00184; A61B 2018/0016;
(Continued)

(56) References Cited

U.S. PATENT DOCUMENTS 3,505,993 A   4/1970 Lewes et al.
4,985,027 A   1/1991 Dressel
(Continued)

FOREIGN PATENT DOCUMENTS

DE   19929713 A1   1/2001
EP   0226336 A2   6/1987
(Continued)

OTHER PUBLICATIONS

Arnoczky et al., Thermal Modification of Connective Tissues: Basic Science Consideration and Clinical Implications, Journal of the American Academy of Orthopedic Surgeons, vol. 8, No. 5, Sep./Oct. 2000.*
(Continued)

*Primary Examiner* — Ahmed M Farah
(74) *Attorney, Agent, or Firm* — Quarles & Brady LLP

(57) ABSTRACT

The present invention provides improved methods and apparatus for skin treatment and tissue remodeling. The apparatus includes an array of needles that penetrate the skin and serve as electrodes to deliver radio frequency current or other electrical or optical energy into the tissue being treated, causing thermal damage in controlled patterns. The damaged regions promote beneficial results such as uniform skin tightening by stimulation of wound healing and collagen growth.

11 Claims, 4 Drawing Sheets

Related U.S. Application Data continuation of application No. 12/914,201, filed on Oct. 28, 2010, now Pat. No. 9,095,357, which is a division of application No. 11/098,030, filed on Apr. 1, 2005, now Pat. No. 7,824,394.

(60) Provisional application No. 60/558,476, filed on Apr. 1, 2004.

(51) Int. Cl.
*A61M 5/158* (2006.01)
*A61B 5/00* (2006.01)
*A61B 18/00* (2006.01)
*A61B 18/20* (2006.01)
*A61B 18/22* (2006.01)

(52) U.S. Cl.
CPC ... *A61B 5/4893* (2013.01); *A61B 2018/00005* (2013.01); *A61B 2018/0016* (2013.01); *A61B 2018/0019* (2013.01); *A61B 2018/00452* (2013.01); *A61B 2018/143* (2013.01); *A61B 2018/2005* (2013.01); *A61B 2018/2211* (2013.01); *A61M 2202/048* (2013.01)

(58) Field of Classification Search
CPC .. A61B 2018/0019; A61B 2018/00452; A61B 2018/0047; A61B 18/18; A61B 2018/1807; A61B 2018/1869; A61B 2018/1876; A61B 2018/1884; A61B 2018/1892; A61B 2018/2005; A61B 18/20; A61B 18/201; A61B 18/22; A61B 2018/22; A61B 2018/2211; A61B 2018/2227; A61B 2018/2233; A61B 18/14; A61B 2018/1405; A61B 2018/1425; A61B 2018/143; A61B 2018/1467; A61B 2018/1477; A61B 5/48; A61B 5/4887; A61B 5/4893; A61N 5/06; A61N 5/0601; A61N 2005/0612; A61N 5/06132; A61N 5/0616; A61N 2005/0626; A61N 2005/063; A61N 2005/0643; A61N 2005/067; A61M 5/158; A61M 2202/04; A61M 2202/048
USPC ..... 606/9–11, 13–15, 27–29, 31, 32, 41–50; 607/88, 89, 92, 93, 96, 100, 101, 104, 607/105, 108–112, 115, 116; 604/19–22, 604/27, 28; 128/898
See application file for complete search history.

(56) References Cited

U.S. PATENT DOCUMENTS

| | | | |
|---|---|---|---|
| 5,000,752 A | 3/1991 | Hoskin et al. | |
| 5,102,410 A | 4/1992 | Dressel | |
| 5,284,154 A | 2/1994 | Raymond et al. | |
| 5,312,395 A | 5/1994 | Tan et al. | |
| 5,458,596 A | 10/1995 | Lax et al. | |
| 5,569,242 A | 10/1996 | Lax et al. | |
| 5,582,184 A | 12/1996 | Erickson et al. | |
| 5,599,342 A | 2/1997 | Hsia et al. | |
| 5,660,836 A | 8/1997 | Knowlton | |
| 5,697,281 A | 12/1997 | Eggers et al. | |
| 5,697,909 A | 12/1997 | Eggers et al. | |
| 5,707,349 A | 1/1998 | Edwards | |
| 5,755,753 A | 5/1998 | Knowlton | |
| 5,807,385 A | 9/1998 | Keller | |
| 5,814,040 A | 9/1998 | Nelson et al. | |
| 5,861,002 A | 1/1999 | Desai | |
| 5,871,524 A | 2/1999 | Knowlton | |
| 5,919,219 A | 7/1999 | Knowlton | |
| 5,928,158 A | 7/1999 | Aristides | |
| 5,948,011 A | 9/1999 | Knowlton | |
| 5,954,710 A | 9/1999 | Paolini et al. | |
| 5,976,129 A | 11/1999 | Desai | |
| 6,048,352 A | 4/2000 | Douglas et al. | |
| 6,106,516 A | 8/2000 | Massengill | |
| 6,120,519 A | 9/2000 | Weber et al. | |
| 6,206,873 B1 | 3/2001 | Paolini et al. | |
| 6,241,753 B1 | 6/2001 | Knowlton | |
| 6,277,116 B1 * | 8/2001 | Utely | A61B 18/14 606/41 |
| 6,311,090 B1 | 10/2001 | Knowlton | |
| 6,334,856 B1 | 1/2002 | Allen et al. | |
| 6,350,276 B1 | 2/2002 | Knowlton | |
| 6,355,054 B1 * | 3/2002 | Neuberger | A61B 18/203 604/20 |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,405,090 B1 | 6/2002 | Knowlton | |
| 6,413,255 B1 | 7/2002 | Stern | |
| 6,416,531 B2 * | 7/2002 | Chen | A61N 5/0601 128/898 |
| 6,425,912 B1 | 7/2002 | Knowlton | |
| 6,427,089 B1 | 7/2002 | Knowlton | |
| 6,430,446 B1 | 8/2002 | Knowlton | |
| 6,438,424 B1 | 8/2002 | Knowlton | |
| 6,453,202 B1 | 9/2002 | Knowlton | |
| 6,461,378 B1 | 10/2002 | Knowlton | |
| 6,470,216 B1 | 10/2002 | Knowlton | |
| 6,482,204 B1 | 11/2002 | Lax et al. | |
| 6,503,231 B1 | 1/2003 | Prausnitz et al. | |
| 6,562,054 B1 | 5/2003 | Weber et al. | |
| 6,597,946 B2 | 7/2003 | Avrahami et al. | |
| 6,605,079 B2 | 8/2003 | Shanks et al. | |
| 6,605,080 B1 | 8/2003 | Altshuler et al. | |
| 6,611,706 B2 | 8/2003 | Avrahami et al. | |
| 6,615,079 B1 | 9/2003 | Avrahami | |
| 6,708,060 B1 | 3/2004 | Avrahami et al. | |
| 6,711,435 B2 | 3/2004 | Avrahami | |
| 6,723,092 B2 | 4/2004 | Brown et al. | |
| 6,743,211 B1 * | 6/2004 | Prausnitz | A61B 5/14514 604/239 |
| 6,749,624 B2 | 6/2004 | Knowlton | |
| 6,766,202 B2 * | 7/2004 | Underwood | A61B 18/14 128/898 |
| 6,905,497 B2 | 6/2005 | Truckai et al. | |
| 6,997,923 B2 | 2/2006 | Anderson et al. | |
| 7,006,874 B2 | 2/2006 | Knowlton et al. | |
| 7,008,421 B2 | 3/2006 | Daniel et al. | |
| 7,022,121 B2 | 4/2006 | Stern et al. | |
| 7,025,765 B2 | 4/2006 | Balbierz et al. | |
| 7,060,061 B2 | 6/2006 | Altshuler et al. | |
| 7,115,123 B2 | 10/2006 | Knowlton et al. | |
| 7,141,049 B2 | 11/2006 | Stern et al. | |
| 7,189,230 B2 | 3/2007 | Knowlton | |
| 7,217,265 B2 | 5/2007 | Hennings et al. | |
| 7,223,264 B2 | 5/2007 | Daniel et al. | |
| 7,278,991 B2 * | 10/2007 | Morris | A61B 18/1477 606/41 |
| 7,331,953 B2 | 2/2008 | Manstein et al. | |
| 7,422,586 B2 | 9/2008 | Morris et al. | |
| 7,824,394 B2 | 11/2010 | Manstein | |
| 8,608,737 B2 * | 12/2013 | Mehta | A61B 18/1206 606/44 |
| 8,882,753 B2 | 11/2014 | Mehta et al. | |
| 9,095,357 B2 * | 8/2015 | Manstein | A61B 18/1477 |
| 9,877,778 B2 * | 1/2018 | Manstein | A61B 18/1477 |
| 2001/0029373 A1 | 10/2001 | Baker et al. | |
| 2002/0087155 A1 | 7/2002 | Underwood et al. | |
| 2002/0091377 A1 | 7/2002 | Anderson et al. | |
| 2002/0111615 A1 * | 8/2002 | Cosman | A61B 18/1482 606/41 |
| 2002/0115991 A1 | 8/2002 | Edwards | |
| 2002/0120260 A1 | 8/2002 | Morris et al. | |
| 2002/0120263 A1 | 8/2002 | Brown et al. | |
| 2002/0128641 A1 | 9/2002 | Underwood et al. | |

(56) References Cited

U.S. PATENT DOCUMENTS

| | | |
|---|---|---|
| 2002/0138049 A1 | 9/2002 | Allen et al. |
| 2002/0161357 A1 | 10/2002 | Anderson et al. |
| 2003/0130655 A1 | 7/2003 | Woloszko et al. |
| 2003/0144652 A1 | 7/2003 | Baker et al. |
| 2003/0212394 A1 | 11/2003 | Pearson et al. |
| 2003/0216719 A1 | 11/2003 | Debenedictis et al. |
| 2004/0048842 A1 | 3/2004 | McMillan |
| 2004/0073277 A1 | 4/2004 | Geronemus et al. |
| 2004/0267335 A1 | 12/2004 | Tulip et al. |
| 2005/0049582 A1 | 3/2005 | DeBenedictis et al. |
| 2005/0087198 A1 | 4/2005 | Bruno-Raimondi et al. |
| 2005/0137662 A1 | 6/2005 | Morris et al. |
| 2005/0209564 A1 | 9/2005 | Bonner et al. |
| 2005/0209565 A1 | 9/2005 | Yuzhakov et al. |
| 2005/0222555 A1 | 10/2005 | Manstein et al. |
| 2005/0222565 A1 | 10/2005 | Manstein |
| 2006/0004306 A1 | 1/2006 | Altshuler et al. |
| 2006/0004347 A1 | 1/2006 | Altshuler et al. |
| 2006/0009750 A1 | 1/2006 | Altshuler et al. |
| 2006/0020309 A1 | 1/2006 | Altshuler et al. |
| 2006/0058712 A1 | 3/2006 | Altshuler et al. |
| 2006/0122668 A1 | 6/2006 | Anderson et al. |
| 2006/0206110 A1 | 9/2006 | Knowlton et al. |
| 2006/0224148 A1 | 10/2006 | Cho et al. |
| 2006/0253112 A1 | 11/2006 | Suarez et al. |
| 2006/0293722 A1 | 12/2006 | Slatkine et al. |
| 2007/0010811 A1 | 1/2007 | Stern et al. |
| 2007/0073367 A1 | 3/2007 | Jones et al. |
| 2007/0106143 A1 | 5/2007 | Flaherty |
| 2007/0173799 A1 | 7/2007 | Hsia |
| 2007/0198003 A1 | 8/2007 | Domankevitz et al. |
| 2007/0208340 A1 | 9/2007 | Ganz et al. |
| 2008/0082090 A1 | 4/2008 | Manstein |
| 2008/0125775 A1* | 5/2008 | Morris .............. A61B 18/1477 606/50 |
| 2008/0221649 A1 | 9/2008 | Echague et al. |
| 2008/0312647 A1* | 12/2008 | Knopp ................ A61B 18/203 606/41 |
| 2009/0124958 A1 | 5/2009 | Li et al. |
| 2010/0010480 A1* | 1/2010 | Mehta .................. A61B 18/14 606/9 |
| 2011/0046615 A1 | 2/2011 | Manstein |

FOREIGN PATENT DOCUMENTS

| | | |
|---|---|---|
| JP | 2000342617 A | 12/2000 |
| JP | 2001510702 A | 8/2001 |
| WO | 9904710 A1 | 2/1999 |
| WO | 0048644 A2 | 8/2000 |
| WO | 0132073 A2 | 5/2001 |
| WO | 0137728 A1 | 5/2001 |
| WO | 02060523 A2 | 8/2002 |
| WO | 02102265 A1 | 12/2002 |
| WO | 03005919 A1 | 1/2003 |
| WO | 2004086947 A2 | 10/2004 |
| WO | 2005007001 A1 | 1/2005 |
| WO | 2005096979 A1 | 10/2005 |
| WO | 2005096980 A1 | 10/2005 |

OTHER PUBLICATIONS

PCT International Search Report, PCT/US2008/061682, dated Sep. 17, 2008, 3 pages.

PCT International Search Report, PCT/US2010/037950, dated Feb. 1, 2011, 7 pages.

PCT Written Opinion, PCT/US2010/037950, dated Feb. 1, 2011, 5 pages.

Harrington, A Review of IR Transmitting, Hollow Waveguides, Fiber and Integrated Optics, 2000, 19:211-217.

Khan, et al., Intradermally Focused Infrared Laser Pulses: Thermal Effects at Defined Tissue Depths, Lasers in Surgery and Medicine, 2005, 36:270-280.

Manstein, et al., Fractional Photothermolysis: A New Concept for Cutaneous Remodeling Using Microscopic Patterns of Thermal Injury, Lasers in Surgery and Medicine, 2004, 34:426-438.

Tschopp, et al., Comparison of Various Methods of Electromyographic Monitoring of the Recurrent Laryngeal Nerve in Thyroid Surgery, Annals of Otology, Rhinology & Laryngology, 2002, 111(9):811-816.

Urmey, et al., Percutaneous Electrode Guidance: A Noninvasive Technique for Prelocation of Peripheral Nerves to Facilitate Peripheral Plexus or Nerve Block, Regional Anesthesia & Pain Medicine, 2002, 27(3):261-267.

Schott North America Inc., Medical Fiber Optic Components, Hightech Solutions for Health, Product Brochure, 2003, 20 pages.

Deka M.E.L.A. s.r.l., Smartlipo Nd:YAG Laser System for Laserlipolisi, Product Brochure, Copyright Deka 003-8018-04-020 Rev. 1.3, 2 pages.

Deka M.E.L.A. s.r.l., Tri-Active Product Brochure, Copyright Deka 003-8010-04-020 Rev. 2.1, 4 pages.

Lutronic, Infini High Intensity Focused RF, Brochure, 5 pages (From Annex to the Communication of the Minutes of the Oral Proceeding of European Application 05733209.0, dated Mar. 5, 2016).

\* cited by examiner

METHOD AND APPARATUS FOR DERMATOLOGICAL TREATMENT AND TISSUE RESHAPING

RELATED APPLICATIONS

The present application is a continuation of U.S. patent application Ser. No. 14/725,976 filed on May 29, 2015 which is a continuation of U.S. patent application Ser. No. 12/914,201 filed on Oct. 28, 2010 now U.S. Pat. No. 9,095,357, issued on Aug. 4, 2015, is a divisional of U.S. patent application Ser. No. 11/098,030 filed on Apr. 1, 2005, now U.S. Pat. No. 7,824,394, issued on Nov. 2, 2010, and claims priority to U.S. Provisional Application Ser. No. 60/558,476 filed on Apr. 1, 2004. The entire disclosures of each of these applications are incorporated herein by reference.

INCORPORATION BY REFERENCE

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention is directed to an improved method for treatment of skin and other tissues. More specifically, it is directed to a method of fractional wounding using arrays of needles to damage selected regions of the skin or subdermal tissue and thereby promote beneficial results including skin tightening and tissue remodeling.

BACKGROUND OF THE INVENTION

Skin is primarily made of two layers. The outer layer, or epidermis, has a depth of approximately 100 µm. The inner layer, or dermis, has depth of approximately 3000 µm from the outer surface of the skin and is primarily composed of a network of fibrous protein known as collagen.

There is an increasing demand for repair of skin defects, which can be induced by aging, sun exposure, dermatological diseases, traumatic effects, and the like. Aging skin tends to lose its elasticity, leading to increased formation of wrinkles and sagging. Other causes of undesirable wrinkles in skin include excessive weight loss and pregnancy. There are several well-known surgical approaches to improving the appearance of skin that involve incisions being made in the skin followed by the removal of some tissue and rejoining of the remaining tissue. These surgical approaches include facelifts, brow lifts, breast lifts, and "tummy tucks." Such approaches have many negative side effects including scar formation, long healing times, displacement of skin from its original location relative to the underlying bone structure, and nonuniform skin tightening.

Many treatments have been developed that use electromagnetic radiation to improve skin defects by inducing a thermal injury to the skin, which results in a complex wound healing response of the skin. This leads to a biological repair of the injured skin and may be accompanied by other desirable effects. Various techniques providing this objective have been introduced in recent years. The different techniques can be generally categorized in two groups of treatment modalities: ablative laser skin resurfacing ("LSR") and non-ablative collagen remodeling ("NCR"). The first group of treatment modalities, LSR, includes causing fairly extensive thermal damage to the epidermis and/or dermis, while the second group, NCR, is designed to avoid thermal damage of the epidermis.

LSR is considered to be an effective laser treatment for repairing skin. In a typical LSR procedure, shown schematically in FIG. 1, a region of the epidermis 100 and a corresponding region of the dermis 110 beneath it are thermally damaged to promote wound healing. Electromagnetic energy 120 is directed towards a region of skin, ablating the skin and removing both epidermal and dermal tissue in region 130. LSR with pulsed $CO_2$ or Er:YAG lasers, which may be referred to in the art as laser resurfacing or ablative resurfacing, is considered to be an effective treatment option for signs of photo aged skin, chronically aged skin, scars, superficial pigmented lesions, stretch marks, and superficial skin lesions. However, patients may experience major drawbacks after each LSR treatment, including edema, oozing, and burning discomfort during first fourteen (14) days after treatment. These major drawbacks can be unacceptable for many patients. A further problem with LSR procedures is that the procedures are relatively painful and therefore generally require an application of a significant amount of analgesia. While LSR of relatively small areas can be performed under local anesthesia provided by injection of an anestheticum, LSR of relatively large areas is frequently performed under general anesthesia or after nerve blockade by multiple injections of anesthetic.

A limitation of LSR is that ablative resurfacing in areas other than the face generally have a greater risk of scarring because the recovery from skin injury within these areas is not very effective. Further, LSR techniques are better suited for correction of pigmentation defects and small lesions than for reducing or eliminating wrinkles.

In an attempt to overcome the problems associated with LSR procedures, several types of NCR techniques has emerged. These techniques are variously referred to in the art as non-ablative resurfacing, non-ablative subsurfacing, or non-ablative skin remodeling. NCR techniques generally utilize non-ablative lasers, flashlamps, or radio frequency current to damage dermal tissue while sparing damage to the epidermal tissue. The concept behind NCR techniques is that thermal damage of the dermal tissue is thought to induce collagen shrinkage, leading to tightening of the skin above, and stimulation of wound healing which results in biological repair and formation of new dermal collagen. This type of wound healing can result in a decrease of structural damage related to photoaging. Avoidance of epidermal damage in NCR techniques decreases the severity and duration of treatment-related side effects. In particular, post-procedural oozing, crusting, pigmentary changes and incidence of infections due to prolonged loss of the epidermal barrier function can usually be avoided by using NCR techniques.

In the NCR method of skin treatment, illustrated schematically in FIG. 2, selective portions of dermal tissue 135 within the dermal layer 110 are heated to induce wound healing without damaging the epidermis 100 above. Selective dermal damage that leaves the epidermis undamaged can be achieved by cooling the surface of the skin and focusing electromagnetic energy 120, which may be a laser beam, onto dermal region 135 using lens 125. Other strategies are also applied using nonablative lasers to achieve damage to the dermis while sparing the epidermis in NCR treatment methods. Nonablative lasers used in NCR procedures generally have a deeper dermal penetration depth as compared to ablative lasers used in LSR procedures. Wavelengths in the near infrared spectrum can be used. These wavelengths cause the non-ablative laser to have a deeper penetration depth than the very superficially-absorbed ablative Er:YAG and $CO_2$ lasers. Examples of NCR techniques and apparatus are disclosed by Anderson et al. in U.S. Patent Publication No. 2002/0161357.

While it has been demonstrated that these NCR techniques can assist in avoiding epidermal damage, one of the major drawbacks of these techniques is their limited efficacies. The improvement of photoaged skin or scars after the treatment with NCR techniques is significantly smaller than the improvements found when LSR ablative techniques are utilized. Even after multiple treatments, the clinical improvement is often far below the patient's expectations. In addition, clinical improvement is usually several months delayed after a series of treatment procedures. NCR is moderately effective for wrinkle removal and is generally not effective for dyschromia. One advantage of NCR is that it does not have the undesirable side effects that are characteristic of the LSR treatment, such as the risk of scarring or infection.

Another limitation of NCR procedures relates to the breadth of acceptable treatment parameters for safe and effective treatment of dermatological disorders. The NCR procedures generally rely on an optimum coordination of laser energy and cooling parameters, which can result in an unwanted temperature profile within the skin leading to either no therapeutic effect or scar formation due to the overheating of a relatively large volume of the tissue.

Another approach to skin tightening and wrinkle removal involves the application of radio frequency ("RF") electrical current to dermal tissue via a cooled electrode at the surface of the skin. Application of RF current in this noninvasive manner results in a heated region developed below the electrode that damages a relatively large volume of the dermis, and epidermal damage is minimized by the active cooling of the surface electrode during treatment. This treatment approach can be painful, and can lead to short-term swelling of the treated area. Also, because of the relatively large volume of tissue treated and the need to balance application of RF current with surface cooling, this RF tissue remodeling approach does not permit fine control of damage patterns and subsequent skin tightening. This type of RF technique is monopolar, relying on a remote grounding of the patient to complete the current flow from the single electrode. The current in monopolar applications must flow through the patient's body to the remote ground, which can lead to unwanted electrical stimulation of other parts of the body. In contrast, bipolar instruments conduct the current between two relatively nearby electrodes through a more localized pathway.

In view of the shortcomings of the above methods of dermatological treatment and tissue remodeling, there is a need to provide a procedure and apparatus that combine safe and effective treatment for tissue remodeling, skin tightening, and wrinkle removal with minimal side effects, such as intra-procedural discomfort, post-procedural discomfort, lengthy healing time, and post-procedural infection.

Citation or identification of any document in this application is not an admission that such document is available as prior art to the present invention.

SUMMARY OF THE INVENTION

It is therefore one of the objects of the present invention to provide an apparatus and method that combines safe and effective treatment for an improvement of dermatological disorders with minimum side effects. Another object of the present invention is to provide an apparatus and method that promotes skin tightening and wrinkle removal by creation of a pattern of small localized regions of thermal damage within the dermis. Still another object of the present invention is to provide a method and apparatus for skin tightening or other forms of tissue remodeling by using an array of electrode needles to controllably deliver electrical or thermal energy to predetermined locations within the dermis or other tissue.

These and other objects can be achieved with an exemplary embodiment of the apparatus and method according to the present invention, in which portions of a target area of tissue are be subjected electromagnetic radiation, such as radio frequency pulses, or thermal energy. Electromagnetic radiation is directed to portions of a target area within the skin or deeper tissue using minimally invasive methods, causing fractional wounding of the portions of the target area. The electromagnetic radiation may be generated by an electromagnetic radiation source, which is configured to deliver heat, radio frequency pulses, electrical current, or the like to a plurality of target areas.

In yet another exemplary embodiment according to the present invention, an electromagnetic radiation source is configured to generate electromagnetic radiation, and a delivery device comprising an array of needles, coupled to the electromagnetic radiation source, is configured to penetrate the skin to a desired depth to deliver the electromagnetic radiation directly to a plurality of target areas.

One method in accordance with the present invention comprises inserting an array of needles into a region of skin to a predetermined depth. Radio frequency pulses of electrical current are then applied to one or more of the needles, which can function as electrodes in monopolar or bipolar modes to create regions of thermal damage and/or necrosis in the tissue surrounding the tips of the needles.

In an alternate aspect of the invention, one or more of the needles in the array may be hollow and used to deliver small amounts of analgesic or anesthetic into the region of skin being treated. These hollow needles may be interspersed among the electrode needles in the array, and they may also function as electrodes.

In another embodiment of the invention, the electrode needles may also be connected to a second source of electrical current in the milliampere range. Detection of a nerve close to any of the inserted needles of the array is achieved by sequential application of small currents to the needles in the array and observation of any visible motor response. If a nerve is detected, the nearby needle or needles can be deactivated during the subsequent application of RF current to other electrode needles in the array to avoid damaging the nerve.

In yet another embodiment of the invention, the methods and apparatus described herein can be used to heat portions of cartilage, such as that located in the nose, using a minimally invasive technique, allowing reshaping of the pliant heated cartilage to a desired form.

A further understanding of the nature and advantages of the present invention will become apparent by reference to the remaining portions of the specification and drawings.

BRIEF DESCRIPTION OF THE DRAWINGS

The following detailed description, given by way of example, but not intended to limit the invention solely to the specific embodiments described, may best be understood in conjunction with the accompanying drawings, in which.

Figure 1:
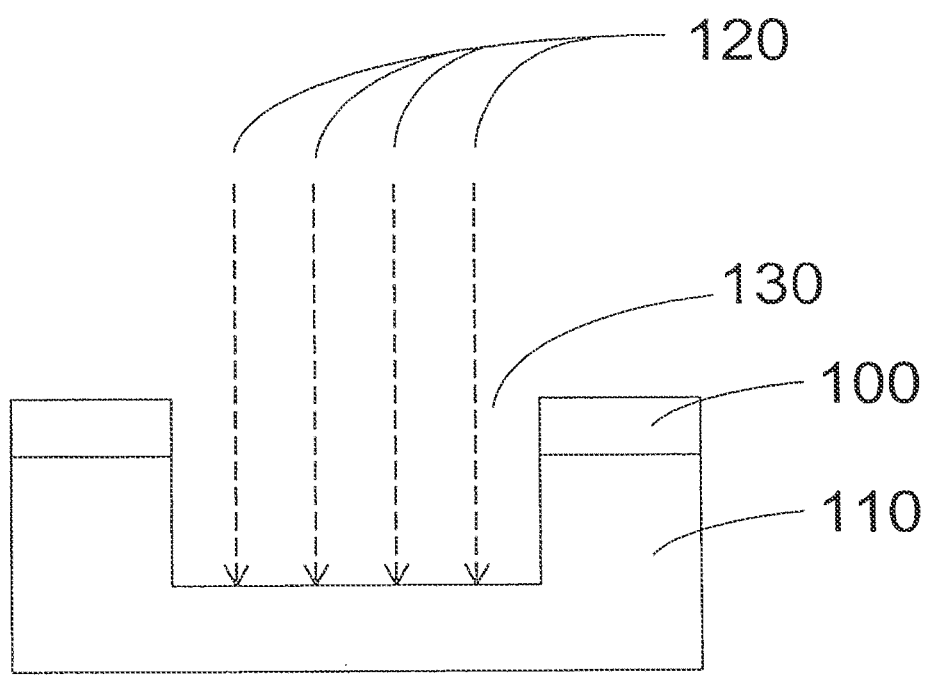
FIG. 1 is a schematic drawing of a cross section of a tissue treated using the ASR method.
Figure 2:
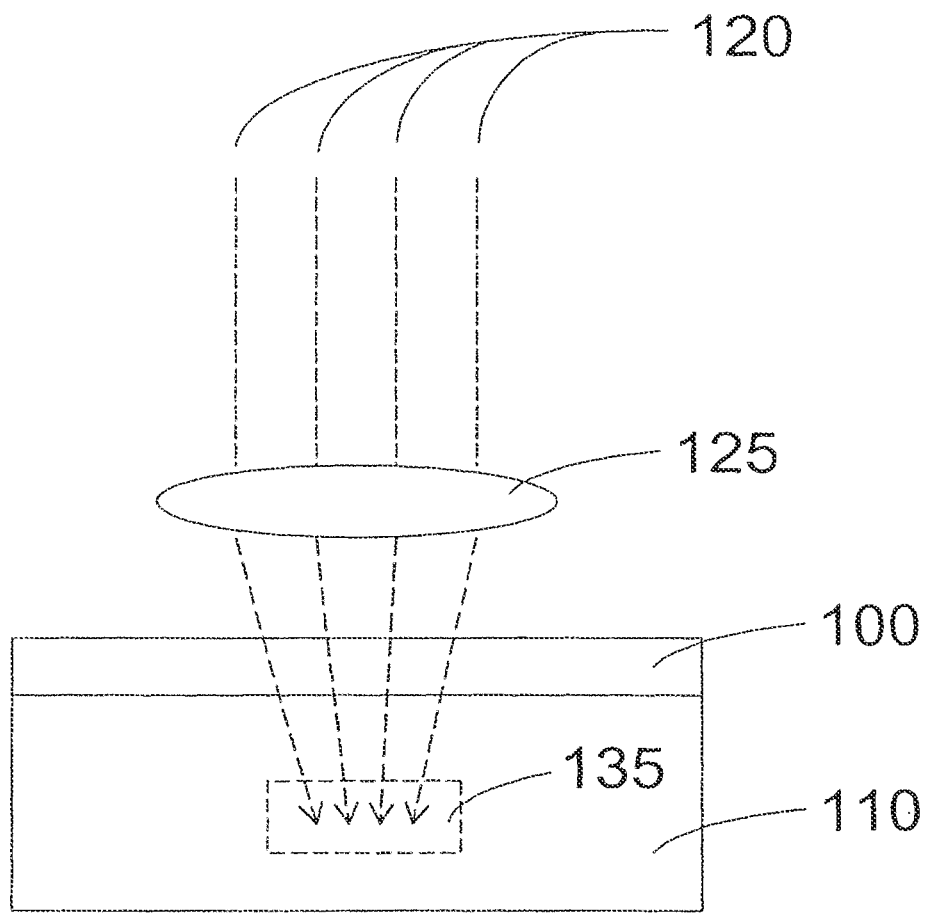
FIG. 2 is a schematic drawing of a cross section of a tissue treated using the NSR method.

Throughout the drawings, the same reference numerals and characters, unless otherwise stated, are used to denote like features, elements, components, or portions of the illustrated embodiments. Moreover, while the present invention will now be described in detail with reference to the Figures, it is done so in connection with the illustrative embodiments and is not limited by the particular embodiments illustrated in the Figures.

DETAILED DESCRIPTION OF THE INVENTION

The present invention relates to methods and apparatus for improvement of skin defects including, but not limited to, wrinkles, stretch marks, and cellulite. In one embodiment, skin tightening or tissue remodeling is accomplished by creating a distribution of regions of necrosis, fibrosis, or other damage in the tissue being treated. The tissue damage is achieved by delivering localized concentrations of electrical current that is converted into heat in the vicinity of the tips of the electrode needles. Inducing regions of local thermal damage within the dermis results in an immediate shrinking of collagen, leading to beneficial skin tightening response. Additionally, the thermal damage tends to stimulate the formation of new collagen, which makes the local skin tissue fuller and gradually leads to additional skin tightening and reduction of wrinkles.

Figure 3:
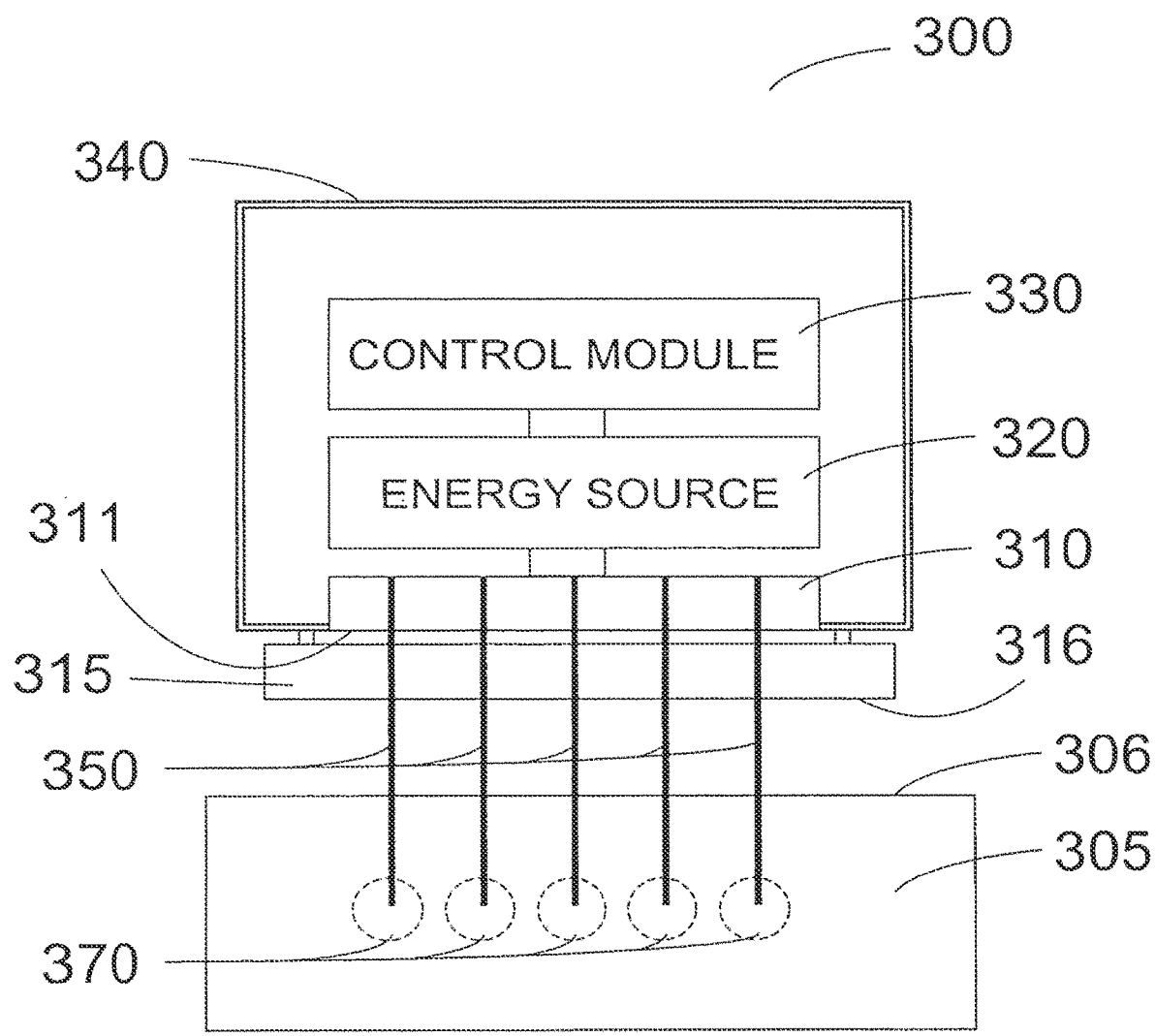
FIG. 3 is a schematic illustration of an apparatus for conducting tissue reshaping using electromagnetic energy according to one embodiment of the present invention.

In an exemplary embodiment of the present invention, tissue treatment apparatus 300 shown in FIG. 3 may be used to create regions of damage within the tissue being treated. The tissue reshaping apparatus may comprise a plurality of needles 350 attached to a base 310. The base is attached to housing 340 or formed as a part of the housing. A source of RF current 320 is electrically connected to each of the needles 350. A control module 330 permits variation of the characteristics of the RF electrical current, which can be supplied individually to one or more of the needles. Optionally, energy source 320 and/or control module 330 may be located outside of the housing.

In one exemplary embodiment, the energy source 320 is a radio frequency (RF) device capable of outputting signals having frequencies in a desired range. In another exemplary embodiment, the energy source is capable of outputting an AC or DC electric current. The control module 330 provides application-specific settings to the energy source 320. The energy source 320 receives these settings, and generates a current directed to and from specified needles for selectable or predetermined durations, intensities, and sequences based on these settings.

In yet another embodiment of the present invention, a spacer substrate 315 containing a pattern of small holes through which the array of needles protrudes may optionally be provided between the base 310 and the surface of the skin 306. This spacer substrate may be used to provide mechanical stability to the needles. Optionally, this substrate may be movably attached to the base 310 or housing 340 and adjustable with respect to base 310, supporting the array of needles to control the depth of the needles protruding from the lower surface 316 of spacer substrate 315, and thus controlling the depth to which the needles are inserted into the skin.

In practicing a method in accordance with the present invention, the sharp distal ends of needles 350 pierce the surface 306 of skin tissue 305 and are inserted into the tissue until the bottom surface 316 of spacer substrate 315 (or the bottom surface 311 of base 310 if a spacer substrate 315 is not used) contacts the surface 306 of the skin 305. This configuration permits reliable insertion of the array of needles to a predetermined depth within the tissue being treated. Control module 330 is then configured to deliver controlled amounts of RF current to one or more needles 350.

Base 310 and/or spacer substrate 315, if used, can be planar or they may have a bottom surface that is contoured to follow the shape of the region of tissue being treated. This permits penetration of the needle array to a uniform depth within the targeted tissue even if the surface of the skin is not planar, e.g., along the eye sockets.

In another embodiment, base 310 and/or a spacer substrate 315, if used, may be cooled by any suitable means (such as by embedded conduits containing circulating coolant or by a Peltier device) to cool the surface of the skin when the needle array penetrates the skin to reduce or eliminate pain. The surface region of the skin being treated and/or the needles themselves may also be precooled by separate means, including convective or conductive means, prior to penetration of the skin by the array of needles.

In a preferred embodiment of the present invention, the shafts of conductive needles 350 are electrically insulated except for the portion of the needle near the tip. In the apparatus of FIG. 3, application of RF current to the needles 350 causes heating in the exposed tip region, inducing thermal damage regions 370 around the tip of each needle. Thermal damage regions 370 result from operation of the apparatus in monopolar configuration, in which a remote grounding electrode, not shown in FIG. 3, is attached to a remote part of the patient's body to complete the circuit of electricity conveyed to needles 350 by energy source 320. In this monopolar configuration, RF current causes heating of the tip regions of the needles 350, generating thermal damage in tissue regions 370 adjacent to the needle tips that are approximately spherical or slightly elongated in shape.

In one embodiment of the invention, current may be delivered simultaneously to all needles in the array to produce a pattern of thermal damage around the tip of each needle. In alternative embodiments, control module 330 and energy source 320 can be configured to supply electrical current to individual needles, to specific groups of needles within the array, or to any combination of individual needles in any desired temporal sequence. Providing current to different needles at different times during treatment (instead of heating all needles in the array at once) may help to avoid potential local electrical or thermal interactions among needles that can lead to excessive local damage.

In yet another embodiment of the present invention one or more vibrating means, such as a piezoelectric transducer or a small motor with an eccentric weight fixed to the shaft, may be mechanically coupled to housing 340 and/or base 310 that supports the array of needles 350. Vibrations conductively induced in needles 350 by such vibrating means can facilitate the piercing of the skin by the needle tips and subsequent insertion of the needles into the tissue.

The vibrating means can have an amplitude of vibration in the range of about 50-500 μm or, more preferably, between about 100-200 μm. The frequency of the induced vibrations can be from about 10 hz to about 10 khz, more preferably from about 500 hz to about 2 khz, and even more preferably about 1 khz. The particular vibration parameters chosen may depend on the size and material of the needles, the number of needles in the array, and the average spacing of the needles. The vibrating means may further comprise an optional controller capable of adjusting the amplitude and/or frequency of the vibrations.

Figure 4:
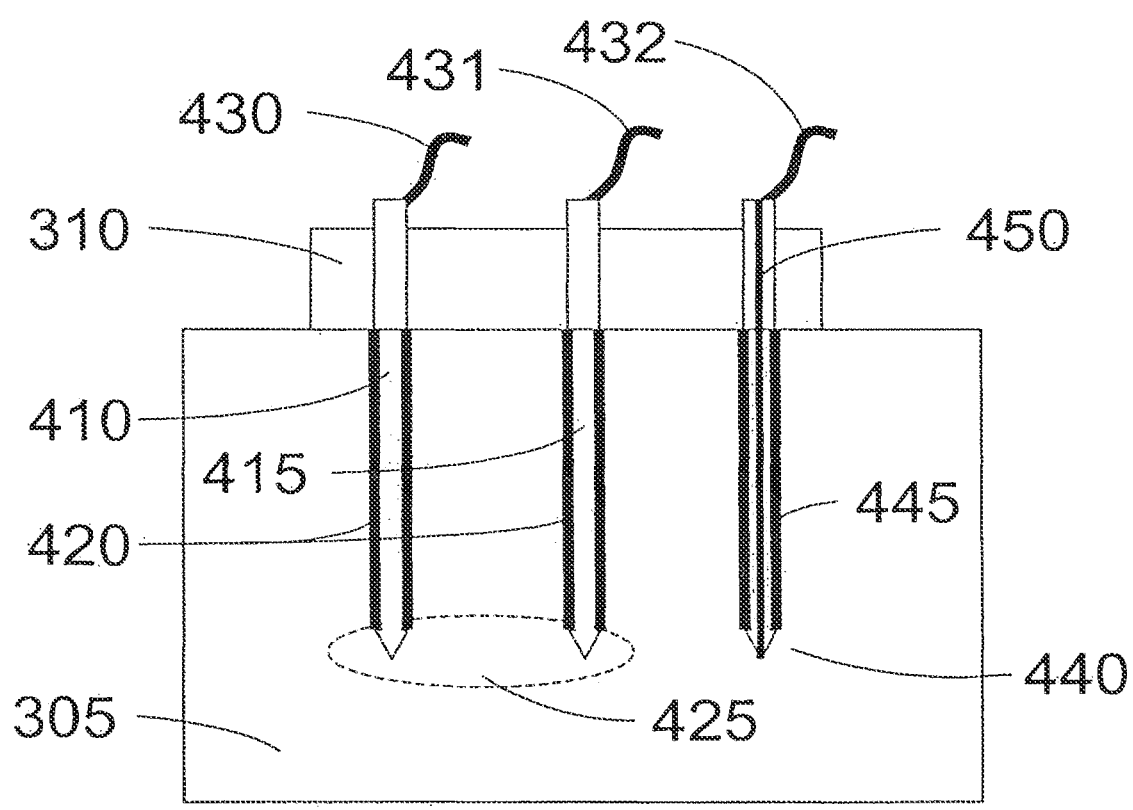
FIG. 4 is a schematic illustration of portions of an apparatus for conducting tissue reshaping according to one embodiment of the present invention.

Additional details and embodiments of the present invention are shown in FIG. 4. Conductive needles 410 and 415 are shown attached to base 310. Insulation 420 covers the shaft of needles 410 and 415 protruding from base 310 except for the region near the lower tip, and electrically insulates each conductive needle shaft from surrounding tissue 305. Electrical conductors 430 and 431, which may be wires or the like, extend from an upper portion of needles 410 and 415 respectively, and are connected to the energy source (not shown here). Suitable insulating materials for insulation 420 include, but are not limited to, Teflon®, polymers, glasses, and other nonconductive coatings. A particular material may be chosen as an insulator to facilitate penetration and insertion of needles 410 and 415 into tissue 305.

Needles 410 and 415 are shown operating in bipolar mode in another embodiment of the present invention. Needle 410 is a positive electrode delivering RF or other current to the tip region of the needle from the energy source via conductor 430. Needle 415 functions as a grounding electrode that is connected to the ground of the energy source via conductor 431. In this configuration the applied current will travel through the tissue between the tips of needles 410 and 415, generating an elongated region of thermal damage 425 around and between the tips of the two needles.

An elongated region of damaged tissue 425 can be created between any two adjacent or nearby needles in the array through proper configuration of control module 330 and energy source 320. In an embodiment of the present invention, elongated damage regions 425 are formed between several pairs of needles within the array of needles to form a desired damage pattern in the tissue 305. The regions of thermal damage 325 created in bipolar operation of the apparatus may be formed simultaneously or, alternatively, sequentially, using any combinations of proximate needles in the array to form each region. A wide variety of thermal damage patterns can be created using a single array of needles through appropriate configuration of energy source 320 and control module 330 to deliver predetermined amounts of current between selected pairs of needles. This apparatus thus allows for the creation of complex damage patterns within the tissue 305 that may be macroscopically elongated in preferred directions to produce anisotropic shrinkage and reshaping.

In practicing the methods and apparatus of the present invention, the needles can have a width of about 500-1000 μm or preferably about 700-800 μm. Needles less than 500 μm in diameter may also be used if they are mechanically strong enough. Needles thicker than about 1000 μm in diameter may be undesirable because of the difficulty in forcing larger needles to penetrate the skin and because of the increased propensity for pain and scarring. The length of the needles extending into the skin will depend on the targeted depth for damaging the tissue. A typical depth for targeting collagen in the dermis is about 1500-2000 μm, although shallower or deeper distances may be preferred for different treatments and regions of the body being treated. Needles within a single array may protrude by different lengths from the base 310 or spacer substrate 315. This will cause the tips of the needles to be positioned at different depths within the tissue being treated, and allow creation of damaged tissue at more than one depth. This variation in needle depth can achieve formation of damaged tissue over a larger volume within the tissue being treated.

The needle arrays may have any geometry appropriate for the desired treatment being performed. The spacing between adjacent needles is preferably greater than about 1 mm apart, and may be as large as about 2 cm. The spacing between needles in an array need not be uniform, and can be closer in areas where a greater amount of damage or more precise control of damage in the target area of tissue is desired. In one embodiment, the array of needles may comprise pairs of needles separated from adjacent pairs by larger distances. This geometry may be well-suited for inducing damage in bipolar mode between pairs of needles. Needles may also be arranged in a regular or near-regular square or triangular array. In any array geometry, the pattern of damage and resultant tissue reshaping may be controlled with some precision by adjusting the intensity and duration of power transmitted to single needles or pairs of needles.

The amount of energy directed to a given needle will vary depending on the tissue being treated and the desired extent of thermal damage to induce. For typical needle spacings noted above, the energy source should be configured to deliver about 1-100 mJ per needle or pair of needles in the array. It may be preferable to initially use lower amounts of energy and perform two or more treatments over the same target area to better control the damage patterns and extent of reshaping.

In yet another embodiment of the present invention, one or more of the needles in the array may be hollow, such as needle 440 in FIG. 4. Center channel 450 may be used to deliver a local analgesic such as lidocaine 2% solution from a source (not shown) located within or above base 310 into the tissue 305 to reduce or eliminate pain caused by the thermal damage process.

In yet another embodiment of the present invention, hollow needle 440 is bifunctional, capable of conducting RF current or other energy via conductor 432 and also capable of delivering a local analgesic or the like through center channel 450. Similar to needles 410 and 415, bifunctional needle 440 has insulation 445 covering the shaft extending from base 310 except for the region near the lower tip. Analgesic may be supplied to the tissue either before or during application of RF or other current to the needle 450.

In one embodiment of the invention, one or more of the needles in the array may be bifunctional like needle 440. Alternatively, one or more needles may be hollow and optionally nonconductive, suitable only for delivering a local analgesic or the like. The array of needles used for a given application may comprise any combination of solid electrodes, bifunctional needles, or hollow nonconductive needles. For example, one type of needle array may comprise pairs of electrode needles operating in bipolar mode, with a hollow needle located between each pair. In this configuration, the hollow needle can deliver analgesic to the tissue between the tips of the electrode needles prior to applying current to the electrodes and causing thermal damage in the numbed tissue.

In yet another embodiment of the present invention, one or more of the needles in the array may be further connected to an electronic detection apparatus and perform the additional function of a probe to detect the presence of a nerve near the tip. The electronic detection apparatus may comprise a source of electrical current in the milliampere range and control means to send small currents on the order of a milliamp to specific needles in the array. Detection of a nerve close to any of the inserted needles of the array is performed by sequential application of small currents to the needles in the array and observation of any visible motor response. If a nerve is detected, control module 330 can be configured to deactivate the needle or needles close to the nerve during the subsequent treatment to avoid damaging the nerve. A nerve detection method based on principles similar to those described herein is disclosed by Urmey et al. in Regional Anesthesia and Pain Medicine 27:3 (May-June) 2002, pp. 261-267.

In still another embodiment, one or more of the needles may be hollow, and a light fiber or light guide is inserted into the hollow needle such that one end of it extends to or slightly protrudes from the needle tip. The other end of the light fiber or light guide in communication with a source of optical energy. Optical energy supplied to the tip of the light guide or light fiber may then be used to heat the tip, which then heats the surrounding tissue, i.e., the target area, to cause fractional wounding at the needle tip. An array of needles used in accordance with the present invention may comprise a mix of electrode needles and light-guide needles. Alternatively, each needle may carry a light guide and all of the energy used to cause thermal damage may be generated by the optical energy source instead of using RF or other electrical current. A portion of the light guide or light fiber, such as the portion at the tip of the needle, may be configured to absorb energy and facilitate conversion of the optical energy to heat. In these embodiments, the optical energy source may comprise, but is not limited to, a diode laser, a diode-pumped solid state laser, an Er:YAG laser, a Nd:YAG laser, an argon-ion laser, a He—Ne laser, a carbon dioxide laser, an eximer laser, or a ruby laser. The optical energy conveyed by a light guide or light fiber may optionally be continuous or pulsed.

Treatments performed in accordance with the present invention may be used to target collagen in the dermis. This can lead to immediate tightening of the skin and reduction of wrinkles overlying the damaged tissue arising from contraction of the heated collagen. Over time, the thermal damage also promotes the formation of new collagen, which serves to smooth out the skin even more.

An alternative application of the methods of the present invention may be to reduce or eliminate the appearance of cellulite. To achieve this, the arrays of needles are configured to target the dermis and optionally the upper layer of subcutaneous fat directly. Creating dispersed patterns of small thermally-damaged regions in these layers can tighten the networked collagen structure and suppress the protrusion of the subcutaneous fat into the dermal tissue that causes cellulite.

Yet another application of the methods and apparatus of the present invention is to reshape cartilage. It is known that cartilage softens upon heating, and heating it to about 70 degrees C. can soften the cartilage sufficiently to permit reshaping that persists upon cooling. Currently, specialized lasers are used to heat and soften cartilage in the nasal passages for reshaping. Using the methods and apparatus described herein, cartilage can be targeted by an array of needles and heated in a suitably gradual way, using lower power densities and longer times, to provide relatively uniform heating. Shaping of the cartilage is thus possible using a minimally invasive technique that can be used where laser heating may not be feasible.

Any of the thermal damaging and tissue reshaping methods practiced in accordance with the present invention may be performed in a single treatment, or by multiple treatments performed either consecutively during one session or at longer intervals over multiple sessions. Individual or multiple treatments of a given region of tissue can be used to achieve the appropriate thermal damage and desired cosmetic effects.

The invention claimed is:

1. A skin treatment method comprising:
   inserting a plurality of needles through a dermal layer of skin and into a subcutaneous fat layer, the plurality of needles being attached to a base, the plurality of needles being further configured to receive at least one of radio frequency (RF), optical, alternating current (AC), or direct current (DC) energy from an energy source;
   regulating delivery of the at least one of RF, optical, AC, or DC energy from the energy source to the plurality of needles to induce thermal damage by the at least one of RF, optical, AC, or DC energy in the subcutaneous fat layer when the needles are inserted therein, wherein the regulating of the delivery of the at least one of RF, optical, AC, or DC energy is configured to cause a dispersed pattern of fractional thermally damaged regions in the subcutaneous fat layer; and
   vibrating at least one of the plurality of needles.

2. The method of claim 1, wherein the plurality of needles are associated with each other in groups of bipolar pairs, wherein regulating the delivery of the at least one of RF, optical, AC, or DC energy includes controlling the at least one of RF, optical, AC, or DC energy being delivered to bipolar pairs to cause areas of non-ablative damage within the subcutaneous fat layer, and wherein each area of non-ablative damage is associated with each bipolar pair of the plurality of needles.

3. The method of claim 1, wherein at least one of the plurality of needles is a mono-polar needle.

4. The method of claim 1, further comprising selecting an application-specific setting for the energy source to cause the energy source to vary at least one of a duration, intensity, and sequence of the at least one of RF, optical, AC, or DC energy transmitted to the plurality of needles based on the selected setting.

5. The method of claim 1, wherein at least two of the plurality of needles have differing lengths.

6. The method of claim 1, further comprising cooling a surface of the skin when inserting the plurality of needles through the dermal layer of skin.

7. The method of claim 1, wherein at least one of the plurality of needles is a hollow needle, and further comprising delivering an analgesic via the hollow needle to tissue surrounding a tip of the hollow needle.

8. The method of claim 1, further comprising detecting, using a detector, a presence of a nerve near a tip of at least one of the plurality of needles.

9. The method of claim 1, wherein inserting the plurality of needles through the dermal layer of skin and into the subcutaneous fat layer comprises passing the plurality of needles through a plurality of holes formed in a spacer disposed between the base and a surface of the dermal layer of skin, wherein the plurality of needles are movable relative to the spacer.

10. The method of claim 1, wherein regulating delivery of at least one of RF, optical, AC, or DC energy further includes inducing damaged regions surrounding each tip of each of the plurality of needles, with undamaged regions between the damaged regions.

11. The method of claim 1, wherein each of the needles has a tip, wherein the pattern of thermally-damaged regions includes at least two adjacent regions of thermal damage, and wherein each adjacent region of thermal damage includes a small localized area of thermal damage surrounding each tip.

* * * * *